(12) United States Patent
Andreina et al.

(10) Patent No.: US 12,335,419 B2
(45) Date of Patent: Jun. 17, 2025

(54) METHOD AND DISTRIBUTED LEDGER SYSTEM FOR SUPPORTING SHARING OF DIGITAL HEALTH DATA OF TRAVELERS IN A TRAVEL ENVIRONMENT

(71) Applicant: NEC Laboratories Europe GmbH, Heidelberg (DE)

(72) Inventors: Sebastien Andreina, Heidelberg (DE); Rahul Bobba, Heidelberg (DE); Ghassan Karame, Heidelberg (DE)

(73) Assignee: NEC CORPORATION, Tokyo (JP)

( * ) Notice: Subject to any disclaimer, the term of this patent is extended or adjusted under 35 U.S.C. 154(b) by 313 days.

(21) Appl. No.: 18/027,638

(22) PCT Filed: Dec. 15, 2020

(86) PCT No.: PCT/EP2020/086287
§ 371 (c)(1),
(2) Date: Mar. 22, 2023

(87) PCT Pub. No.: WO2022/063420
PCT Pub. Date: Mar. 31, 2022

(65) Prior Publication Data
US 2023/0377700 A1 Nov. 23, 2023

(30) Foreign Application Priority Data
Sep. 24, 2020 (EP) .................................. 20197973

(51) Int. Cl.
*H04L 9/00* (2022.01)
*G06F 16/245* (2019.01)
(Continued)

(52) U.S. Cl.
CPC .............. *H04L 9/50* (2022.05); *G06F 16/245* (2019.01); *G06F 16/27* (2019.01); *G16H 10/40* (2018.01); *G16H 10/60* (2018.01); *H04L 9/3218* (2013.01)

(58) Field of Classification Search
CPC ......... H04L 9/50; H04L 9/3218; G16H 10/40; G16H 10/60
(Continued)

(56) References Cited

U.S. PATENT DOCUMENTS

| 2016/0328713 | A1 | 11/2016 | Ebrahimi |
| 2019/0165943 | A1* | 5/2019 | Chari .................... H04L 9/3221 |

(Continued)

FOREIGN PATENT DOCUMENTS

| JP | 2018516030 A | 6/2018 |
| JP | 2019153130 A | 9/2019 |
| JP | 2020129760 A | 8/2020 |

OTHER PUBLICATIONS

Davison, How blockchain technology can help revive air travel, Jan. 21, 2021,https://forkast.news/how-blockchain-technology-can-help-revive-air-travel/ (Year: 2021).*

*Primary Examiner* — Zi Ye
(74) *Attorney, Agent, or Firm* — Leydig, Voit & Mayer, Ltd.

(57) ABSTRACT

A method for sharing of digital health data in a travel environment is provided. Traveler's identities are managed using a distributed ledger system, that includes a global identity blockchain, security blockchains, and a health blockchain. The method comprises sending a request for predetermined number of health data records, receiving consecutive access keys for the requested records and a zero knowledge proof, verifying the zero knowledge proof, wherein the zero knowledge proof validates a latest access key of the consecutive access keys. Upon verification, (Continued)

retrieving the health data records from the health blockchain based on hashed access keys, wherein the hashed access keys are generated from the consecutive access keys, and verifying the consecutive access keys provided by the traveler using hashed previous access keys included in the retrieved health data records, to determine whether the traveler has provided the access keys required for the retrieved health data records as requested.

17 Claims, 3 Drawing Sheets

(51) Int. Cl.
  *G06F 16/27* (2019.01)
  *G16H 10/40* (2018.01)
  *G16H 10/60* (2018.01)
  *H04L 9/32* (2006.01)

(58) Field of Classification Search
  USPC ............................................. 713/176
  See application file for complete search history.

(56) References Cited

U.S. PATENT DOCUMENTS

2019/0213333 A1\* 7/2019 Williams ............ G06F 21/6245
2020/0168307 A1\* 5/2020 Chen ..................... G06F 16/22

\* cited by examiner

METHOD AND DISTRIBUTED LEDGER SYSTEM FOR SUPPORTING SHARING OF DIGITAL HEALTH DATA OF TRAVELERS IN A TRAVEL ENVIRONMENT

CROSS REFERENCE TO RELATED APPLICATIONS

This application is a U.S. National Phase application under 35 U.S.C. § 371 of International Application No. PCT/EP2020/086287, filed on Dec. 15, 2020, and claims benefit to European Patent Application No. EP 20197973.9, filed on Sep. 24, 2020. The International Application was published in English on Mar. 31, 2022 as WO 2022/063420 A1 under PCT Article 21(2).

FIELD

The present invention relates to a method for supporting sharing of digital health data of travelers in a travel environment.

Furthermore, the present invention relates to a distributed ledger system for supporting sharing of digital health data of travelers in a travel environment.

BACKGROUND

For example, airports are very complex systems through which millions of people travel every day. Their complexity has reached a point where a traveler can hardly understand what is going on behind the scenes. What seems a straightforward workflow—drop your luggage at check-in counter, go through metal detectors, board the plane, disembark, retrieve your luggage—is in reality made possible by many processes working in unison to make it all happen. One such process is identity management. Indeed, the identity of every passenger/traveler has to be verified in order to ensure that the traveler is not dangerous, and that the traveler really is who he claims to be. Therefore, at each checkpoint, the traveler has to show some valid ID (e.g., a passport), a valid ticket, and possibly a valid entry visa if the country of destination requires one (e.g., ESTA: Electronic System for Travel Authorization).

Furthermore, in this context and in times of possible pandemics, there can be a demand to get trustful information about the traveler's health, such as to ensure that the traveler is not contagious and/or up to date on her vaccines. Currently, in the midst of the COVID-19 pandemic, many countries require a negative PCR test to be performed less than 48 hours before the departure. However, this may not provide enough information. Furthermore, a false negative test may put in jeopardy the safety of all the passengers. In order to prevent this, many discussions between governments and airline are happening on how passengers can prove their health. One example is the creation of a so called "Health Passport" that would ensure the visiting country about the healthiness of the passengers. This health passport would contain health proofs which are proofs on the validity of the test results performed in a privacy preserving manner, and upon demand, the traveler could reveal the results of the latest tests performed to show the risk of her carrying the virus.

Sharing highly private health information poses unique challenges for individuals, governments and industries. Protecting the privacy of individuals is paramount and it may be intended to address some of the key challenges that may be identified as follows:

Ensuring strong data privacy such as individuals are in full control of their health data. For instance, health data and/or transactions should be unlinkable to the owner by external parties. Furthermore, even in the case where a user shares a part of her data, future data and data insertion should be again fully unlinkable for the individual.

Verifiers of health data such as industries, health and immigration authorities can check the authenticity of health information independently. For instance, the verifier can check if the health data presented actually belongs to the individual presenting the data and that it is not altered nor forged.

Health data is completely presented without omissions. For instance, the individual presenting the data is not able to omit any unfavorable health results. Once an individual consents to sharing the data, they will automatically present the complete and up-to-date data over a period of time (e.g. the lasts two weeks).

In recent years, there is an approach for building and deploying identity solutions pursued by providers in the market such as Sovrin (further information is retrievable at https://sovrin.org) and Evernym (further information is retrievable at https://www.evernym.com). These providers offer solutions based on fully self-sovereign users, i.e. the users are in full control of the data and the proofs that they share and as a consequence they also can choose to not reveal any unfavourable results. Verifiable credentials are elegant for proving static use cases such as proving someone is above a certain age, but face limitations in dynamic use cases such as health data, where the status is constantly evolving.

While fully self-sovereign identities are interesting for the users/travelers, they are not desirable in many use-cases, as they provide the travelers with the possibility to selectively disclose the information they want, which might hide some crucial information, such as a positive test for an infectious disease.

SUMMARY

In an embodiment, the present disclosure provides a method for supporting sharing of digital health data of a plurality of travelers in a travel environment, wherein an identity of a traveler is managed using a distributed ledger system, wherein the distributed ledger system includes a global identity blockchain, several security blockchains and a health blockchain, wherein the global identity blockchain is employed as a registry to authenticate entities of the distributed ledger system, wherein a security blockchain of the several security blockchains is employed for a predetermined travel segment, such that the security blockchain is accessible by entities of the distributed ledger system that are involved in the predetermined travel segment, wherein the health blockchain is employed for sharing health data of the travelers in a key-value store of the health blockchain, wherein a health data record is stored against a hashed access key, wherein the health data record includes a hashed previous access key and health data information. The method comprises: sending, from the security blockchain to a traveler, a request to share a predetermined number of health data records; receiving, by the security blockchain, consecutive access keys for the requested health data records and a zero knowledge proof from the traveler; verifying, by the security blockchain, the zero knowledge proof received from the traveler, wherein the zero knowledge proof is utilized to validate a latest access key of the consecutive access keys provided by the traveler; upon successful verification of the zero knowledge proof, retrieving, by the security blockchain, the health data records from the health blockchain based on hashed access keys, wherein the hashed access keys are generated from the access keys provided by the traveler; and verifying, by the security blockchain, the access keys provided by the traveler using hashed previous access keys included in the retrieved health data records, in order to determine whether the traveler has provided the access keys required for the health data records as requested.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
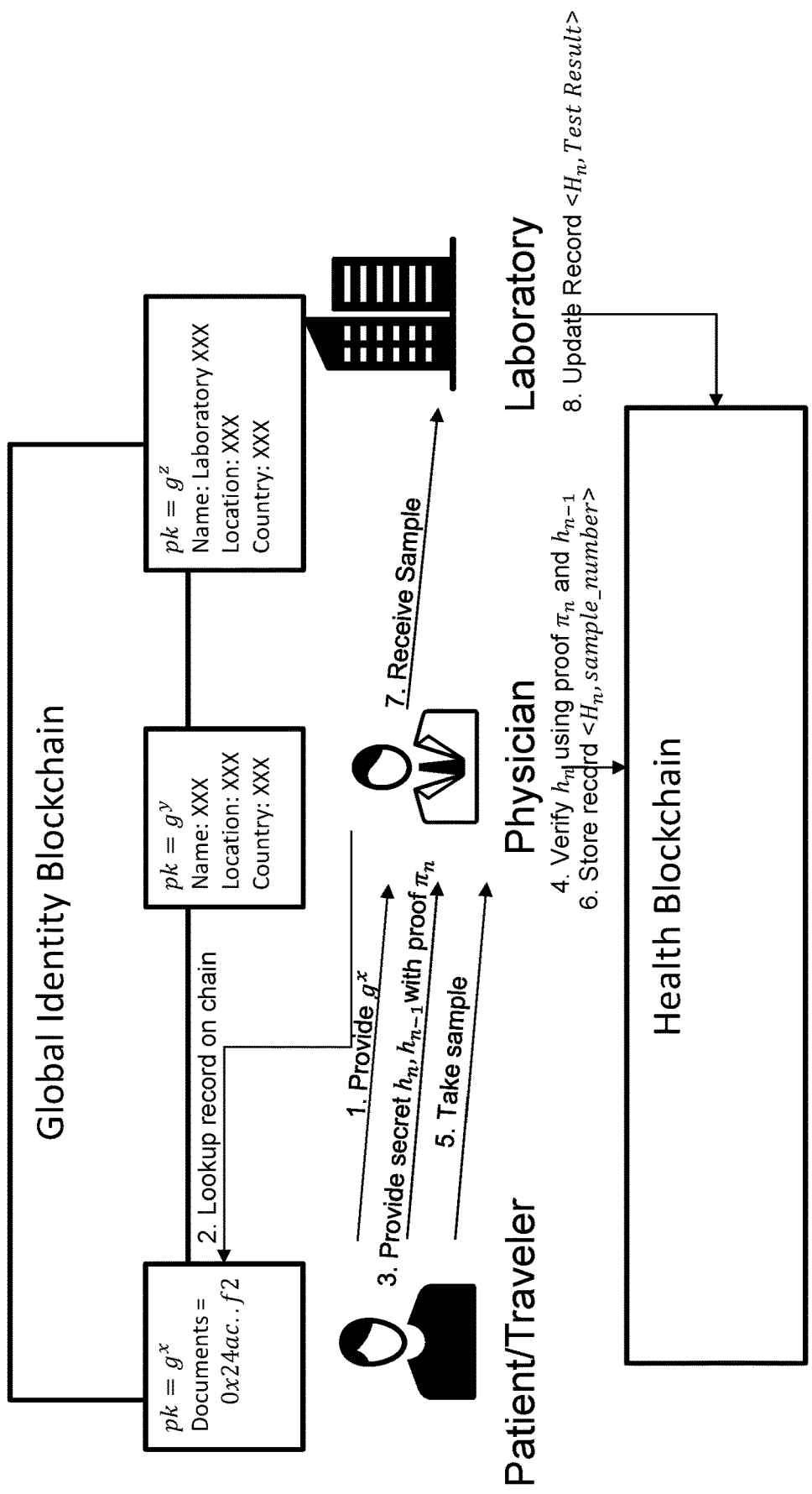
FIG. 1 is a schematic view illustrating a workflow for a method according to an embodiment of the invention.

In an embodiment, the present invention the present invention to improves and further develops a method and a system of the initially described type for supporting sharing of digital health data of travelers in a travel environment in such a way that privacy for the traveler is provided, while improving the provision of some security to the different entities.

In an other embodiment, the present invention provides a method for supporting sharing of digital health data of travelers in a travel environment, wherein the travelers' identity is managed using a distributed ledger system, wherein the distributed ledger system includes a global identity blockchain, several security blockchains and a health blockchain, wherein the global identity blockchain is employed as a registry to authenticate entities of the distributed ledger system, wherein a security blockchain is employed for a predetermined travel segment, such that the security blockchain is accessible by entities of the distributed ledger system that are involved in the predetermined travel segment, wherein the health blockchain is employed for sharing health data of the travelers in a key-value store of the health blockchain, wherein a health data record is stored against a hashed access key, wherein the health data record includes a hashed previous access key and health data information, the method comprising:

Sending, from a security blockchain to a traveler, a request to share a predetermined number of health data records;

Receiving, by the security blockchain, consecutive access keys for the requested health data records and a zero knowledge proof from the traveler;

Verifying, by the security blockchain, the zero knowledge proof received from the traveler, wherein the zero knowledge proof is utilized to validate a latest access key of the access keys provided by the traveler;

Upon successful verification of the zero knowledge proof, retrieving, by the security blockchain, the health data records from the health blockchain based on hashed access keys, wherein the hashed access keys are generated from the access keys provided by the traveler;

Verifying, by the security blockchain, access keys provided by the traveler using hashed previous access keys included in the retrieved health data records, in order to check whether the traveler has provided the access keys required for the health data records as requested.

Furthermore, in an embodiment, the present invention provides a distributed ledger system for supporting sharing of digital health data of travelers in a travel environment, wherein the distributed ledger system includes a global identity blockchain, several security blockchains and a health blockchain, wherein the global identity blockchain is employed as a registry to authenticate entities of the distributed ledger system, wherein a security blockchain is employed for a predetermined travel segment, such that the security blockchain is accessible by entities of the distributed ledger system that are involved in the predetermined travel segment, wherein the health blockchain is employed for sharing health data of the travelers in a key-value store of the health blockchain, wherein a health data record is stored against a hashed access key, wherein the health data record includes a hashed previous access key and health data information, wherein a security blockchain is configured to send to a traveler a request to share a predetermined number of health data records, wherein the security blockchain is configured to receive consecutive access keys for the requested health data records and a zero knowledge proof from the traveler, wherein the security blockchain is configured to verify the zero knowledge proof received from the traveler, wherein the zero knowledge proof is utilized to validate a latest access key of the access keys provided by the traveler, wherein, upon successful verification of the zero knowledge proof, the security blockchain is configured to retrieve the health data records from the health blockchain based on hashed access keys, wherein the hashed access keys are generated from the access keys provided by the traveler, wherein the security blockchain is configured to verify access keys provided by the traveler using hashed previous access keys included in the retrieved health data records, in order to check whether the traveler has provided the access keys required for the health data records as requested.

According to the present invention, it has first been recognized that an enormous improvement in the context of sharing digital health data of travelers in a travel environment can be achieved by providing range query over unlinkable sequential health data of the traveler stored on a specific health blockchain. According to the invention, a distributed ledger system is used, which includes a global identity blockchain, several security blockchains and a health blockchain. The travelers' identity is managed using the distributed ledger system. The global identity blockchain is employed as a registry to authenticate entities/actors of the distributed ledger system. Thus, the global identity blockchain is accessible by all entities/actors of the distributed ledger system, such that the entities/actors are registered and authenticated on the global identity blockchain. With regard to the security blockchains a security blockchain is employed for a predetermined travel segment, such that the security blockchain is accessible only by entities of the distributed ledger system that are involved in the predetermined travel segment. The health blockchain is employed for sharing health data records of the travelers in a key-value store of the health blockchain. A health data record is stored against a hashed access key, wherein the health data record includes a hashed previous access key and health data information as value in the key-value store of the health blockchain.

Taken this configuration into consideration, according to the invention, a security blockchain sends to a traveler a request to share a predetermined number of the latest health data records. Then, the traveler sends to the security blockchain consecutive access keys for the requested health data records together with a zero knowledge proof for the access keys. The security blockchain verifies the zero knowledge proof received from the traveler, wherein the zero knowledge proof is utilized to validate a latest (newest) access key of the access keys provided by the traveler, which has not yet been linked in the health blockchain. In this regard, the latest (newest) access key having not yet been linked in the health blockchain means that a hash of this latest access key has not yet been inserted/recorded in the health blockchain. That is, the zero knowledge proof is utilized to validate the correctness of the new access key to add to the health blockchain. Upon successful verification of the zero knowledge proof, the security blockchain retrieves the health data records from the health blockchain based on hashed access keys. The hashed access keys are generated from the access keys provided by the traveler using a predetermined hash function. Then, the security blockchain verifies the (remaining) access keys provided by the traveler, which have been already linked in the health blockchain. In this regard, the access keys having been already linked in the health blockchain means that hashes of these access keys have been already inserted/recorded in the health blockchain. The verification of the remaining access keys is done through deriving the actual stored key using a one way function such as a Hash function. The value associated with the derived key can then be retrieved in the health blockchain, which further provides information to verify the link with the previous derived keys. Thus, the verification can be done using the hashed previous access keys that are included in the retrieved health data records. Hence, it can be checked and ensured that the traveler has provided all access keys required for all the health data records as requested by the security blockchain. The health blockchain does not have any interpretable links. However, there is a hidden hash chain, such that one can see the link only when one possess the data in order to verify the links stored in the blockchain.

Thus, the present invention provides a method and a system for supporting sharing of digital health data of travelers in a travel environment, wherein the privacy for the traveler is provided, while improving the provision of some security to the different entities.

The travel environment may include but is not limited to airport, train, and/or ship travel (such as ferry and/or cruise ship).

The term "travel segment" may be understood, in particular in the claims, preferably in the description as a term typically applied to portions of an itinerary where the traveler will have a stop in multiple cities along the way. For example, the term travel segment may be or include a flight segment in the context of an airport travel environment. The "flight segment" may be understood as a term typically applied to portions of an itinerary where you will land in multiple cities along the way. However, technically all flights may have at least one flight segment—on a nonstop flight, the segment is from the city where you take off to your final destination. Furthermore, flight segments in air travel may be defined by airlines as all travel, including all legs and stopovers, which are listed under the same flight number on an itinerary. In essence, no matter how many times a passenger boards or gets off the same aircraft, a flight segment may be defined as travel from the time the traveler/passenger initially boards the plane until she disembarks at her destination, as long as it is on the same aircraft and the flight number does not change. The number of segments in her travel plans may be equal to the number of flight numbers on her itinerary.

The terms "entity" and "actor" may be used synonymously and may include in particular in the claims, preferably in the specification, each a device adapted to perform computing like a personal computer, a tablet, a mobile phone, a server, or the like and comprises one or more processors having one or more cores and may be connectable to a memory for storing one or more applications which is/are adapted to perform corresponding steps of one or more of the embodiments of the present invention. Any application may be software-based and/or hardware-based installed in the memory on which the processor(s) can work on. The devices, entities or the like may be adapted in such a way that the corresponding steps to be computed are performed in an optimized way. For instance different steps may be performed in parallel with a single processor on different of its cores. Further the entities may be identical forming a single computing device. The device or devices may also be instantiated as a virtual device running on a physical computing resource. Different devices may therefore be executed on said physical computing resource. In other words the above mentioned terms of "entity" are each to be understood as any kind of physical or virtual computing entity or computing entities and may include, but are not limited to the following: an application running on a computer, a microprocessor, a single, dual, quad or octa-core processor or processors or the like or a computer, processor, or the like with a memory. Said application, computer or processor may have one or more interfaces, ports or the like for communication with other devices, entities, ports, interfaces or the like.

The term "transaction" is to be understood in the most general sense and refers in particular in the claims, preferably in the specification to information sent or transmitted into the network, e.g. to nodes connected to the node sending said transaction. Said transaction may be provided in form of a message, a data packet or the like and may comprise information for the recipients of said transaction.

The term "blockchain" may be understood, in particular in the claims, preferably in the description as a distributed database maintaining a continuously growing list of data records that are hardened against tampering and revision even by operators of the data storing nodes hosting database. A blockchain comprises for example two kinds of records: so-called transactions and so-called blocks. Transactions may be the actual data to be stored in the blockchain and blocks may be records confirming when and in what sequence certain transactions became journaled as a part of the blockchain database. Transactions may be created by participants and blocks may be created by users who may use specialized software or equipment designed specifically to create blocks.

A blockchain may also provide smart contracts capabilities. Smart contracts are pieces of software that run on the blockchain and provide an interface to interact with the data. Smart contracts are typically enforced by the nodes/entities of the distributed ledger system. It is not possible for a single entity to bypass the rules defined by a smart contract, since it would require the agreement of the majority of the participants. The main advantage of smart contracts is that they can automate an organization's business logic. In turn, the switch to automation cancels the effects of human errors and misunderstandings that may lead to legal disputes. A legal contract or a law might be subject to personal interpretations, but software is deterministic; there is no room for subjective interpretations. Smart contracts can be typically issued by any entity in the system, but technology implemented for embodiments of the present invention may empower only a subset of entities to issue smart contracts in the distributed ledger system.

According to embodiments of the invention, it may be provided that a previous access key, which is included as hash (i.e. as hashed previous access key) in a health data record of the traveler, represents the access key for the previous health data record of the traveler on the health blockchain. In this regard, the previous health data record can be addressed by generating a hash of this (previous) access key.

According to embodiments of the invention, a first hash function may be used to compute the hashed access keys that are used as keys for health data records in the key-value store of the health blockchain. A second hash function may be used to compute hashed previous access keys that are stored as values in health data records in the key-value store of the health blockchain. In this regard, two different hash functions Hash and Hash' may be employed, which achieves all the properties of a cryptographic hash function. For example, Hash(x) and Hash'(x) may be instantiated as sha256(x) and sha256("prefix"+x) respectively, for any given "prefix" string. Thus, privacy for the health data of the traveler on the health blockchain may be provided in an efficient way.

According to embodiments of the invention, the traveler may provide a physician entity with secret information and a zero knowledge proof $\pi_n$ for the secret information. Thus, the physician entity can use the zero knowledge proof $\pi_n$ to verify the secret information $h_n$, $h_{n-1}$ provided by the traveler. If the proof is correct, the physician entity can use the secret information $h_n$, $h_{n-1}$ to register a new health data record (i.e. the $n^{th}$ health data record for the traveler) on the health blockchain.

According to embodiments of the invention, the secret information $h_n$, $h_{n-1}$ may include an access key $h_n$ and a previous access key $h_{n-1}$. Both keys can be used to register the new health data record on the health blockchain, wherein a hash $H_n$ of the access key $h_n$ can be used as key in the key-value store of the health blockchain. A hash $H_{n-1}'$ of the previous access $h_{n-1}$ can be used as value in order to establish and deposit a link to the previous health data record in the health blockchain.

According to embodiments of the invention, the physician entity may check and ensure that the secret information $h_n$, $h_{n-1}$ provided by the traveler has not been used yet using the health blockchain. Thus, data integrity of health data to be stored in the health blockchain is supported.

According to embodiments of the invention, it may be provided that a multiplicative cyclic group G of prime order q with public generators g and h is used for sharing health data of the traveler on the health blockchain. A generator (such as g and h) in a cyclic group with an operation * may be an element with the property of iterating through all the elements of the group when subsequently applying the group operation on itself. In other words, every element of the group may be expressed using the generator (i.e. g or h) and the number of time the operation * should be performed (i.e. $g^{1, 2, 3, \ldots}$ or $h^{1, 2, 3, \ldots}$). A private key x of the traveler may be picked as a random $x \in \mathbb{Z}_q$ and a public key of the traveler is $y=g^x$. In this regard, $\mathbb{Z}_q$ may be a multiplicative group of integers that are co-prime with q. The traveler keeps track of a variable n referring to a total number of health data records of the traveler. Thus, the traveler can compute the access key for the nth health data record as $h_n = h^{x^n}$ and a previous access key as $h_{n-1} = h^{x^{n-1}}$ based on the private key x of the traveler. Hence, a secure and privacy preserving handling of the traveler's health data may be provided. Furthermore, with regard to the aforementioned notation as to $h_n$ and $h_{n-1}$, it is noted that generator itself such as h may correspond to $h_0 = h^{x^0} = h^1$, (i.e. when n=0). $h_0$ may be the same for (all) the travelers/users of the distributed ledger system.

According to embodiments of the invention, the zero knowledge proof for the secret information ($h_n$, $h_{n-1}$) provided by the traveler to the physician entity may comprise the following steps:

Generating, by the traveler, commitments $t_h = (h_{n-1})^r$, $t_g = g^{r_1}$ and $t_k = g^{r_2}$ using $r_1$, $r_2$ drawn uniformly at random from $\mathbb{Z}_q$, Sending, by the traveler, the commitments $t_h$, $t_g$ and $t_k$ to the physician entity, Sending, by the physician entity, challenges $c_1$, $c_2$ to the traveler, wherein the physician entity generates the challenges $c_1$ and $c_2$ drawn uniformly at random from $\mathbb{Z}_q$, Sending, by the traveler, responses $s_1$, $s_2$ to the physician entity, wherein the traveler generates the responses $s_1$, $s_2$ as $s_1 = r_1 + c_1 * x$ and $s_2 = r_2 + c_2 x^n$.

Thus, it may be provided that the physician entity accepts the zero knowledge proof, if $g^{s_1}$ is equal to $t_g * y^{c_1}$ and $(h_{n-1})^{s_1}$ is equal to $t_h * (h_n)^{c_1}$ as well as if $h^{s_2}$ is equal to $t_k * (h_n)^{c_2}$. If this is the case, then the physician entity can be ensured that the values $h_n$ and $h_{n-1}$ sent by the traveler as patient are correct. Since $h_n$ is unique for a given private key x, if the physician entity is ensured $h_n$ has been computed correctly, it knows that the traveler/patient is not trying to hide some data.

According to embodiments of the invention, the health blockchain may receive from the physician entity a register transaction for adding a new health data record for the traveler to the health blockchain. The register transaction may comprise a hashed access key, a hashed previous key and health data information. Thus, it may be provided that the new health data record is stored against the hashed access key, wherein the hashed previous key and the health data information is stored as value of the new health data record in the key-value store of the health blockchain. Thus, a secure and privacy preserving handling of the traveler's health data may be provided.

According to embodiments of the invention, it may be provided that the health data information includes a sample number that is used to identify the new health data record. Thus, for instance, a laboratory entity may update the new health data record on the health blockchain. Specifically, the new health data record on the health blockchain may be updated upon receiving an update transaction, e.g. from the laboratory entity, such that the health data record comprises updated health data information for the associated hashed access key. In this regard, a suitable workflow may be performed as follows:

The physician can then take a sample from the patient, i.e. from the traveler;

The sample of the traveler is recorded on the health blockchain using the secret information provided by the traveler and verified beforehand;

The sample of the traveler is sent for analysis to a laboratory, i.e. to a laboratory entity;

The laboratory updates the health data record for the traveler and adds the result of the traveler's test.

According to embodiments of the invention, the health data information of the traveler and/or the updated health data information of the traveler may include information about health data of the traveler. For example, the health data information may include a viral test result, vaccination information, and/or a general medical health test result such as information about viral infection, viral flue, etc.

According to embodiments of the invention, the security blockchain may verify that the health data of the traveler satisfies a predetermined policy setup. For example, the health department of each country might decide on a policy for mandated tests for travelers. Hence, according to an embodiment, the smart contract of the blockchain may use the test output (i.e. the heath data of the traveler) retrieved for each access key from the health blockchain and apply the arrival country's policy to ensure that the traveler performed all the mandated tests. If the traveler's tests match the policy, the traveler is considered as healthy and non-contagious.

According to embodiments of the invention, it may be provided that the consecutive access keys, which are provided by the traveler, represent together with the associated health data records a time frame. Thus, the consecutive access keys represent a list of access keys being sequential without omission. Further, this list of access keys can represent (together with the associated health data records) a time frame to which the information (such as test results) of the health data records refers. Hence, the traveler may effectively create a proof of all his tests were performed over a specific period of time.

According to embodiments of the invention, it may be provided that the physician entity verifies credential information provided by the traveler using the global identity blockchain in order to authenticate the traveler at the physician entity.

At least one embodiment of the invention may consider the following characteristics:

Utilizing zero knowledge proofs in combination with hash chains in a blockchain to realize range queries in $O(\log(n))$ to achieve a trustworthy chain of events without omission between events.

Inserting an empty health data record upon every query and committing that record in the hash chain and including it in the zero knowledge proof to prove "freshness" of the proof.

Embodiments of the invention may allow to perform selected range queries in a privacy-preserving manner from the blockchain. These queries may ensure contiguous responses over a defined period without any gaps in knowledge or any omission of an intermittent record.

Since health proofs of a traveler contain sensitive data on end users, an embodiment of the invention should provide self-sovereign management of this data to each user. Furthermore, as these health proofs need to be trusted by many different governments, it requires a trusted decentralized platform, and therefore aims at the use of a blockchain that would fulfill all the previous requirements. Additional requirements on the embodiment are high level of privacy for the users and high degree of security for the entities requesting the information, as it should not permit end user to cheat. Indeed, since no test has a 100% accuracy, it should not be possible for a person that is sick to perform as many tests as possible until one is falsely negative and only show this one. To this end, the end users is enforced to show all the contiguous tests without omission during a given period of time, effectively providing a certified range query for the given period.

According to an embodiment, the above challenges can be addressed by using blockchain technology and the introduction of a novel zero-knowledge-proof procedure. To illustrate such an embodiment, this may be applied e.g. to the CoVID-19 test processes and how these results could be shared.

Thus, embodiments of the invention describe a privacy preserving solution that permits range query over unlinkable sequential data stored on blockchain using zero knowledge proof. The output of this range query is proved to be sequential (no omission possible) and up to date. Embodiments of the invention can be especially useful in the context of digital health passport in a safe travel system that requires the sharing of test data by travelers to ensure they are not contagious or up to date on their vaccines.

Individual health information is highly private and so far was shared in the state of the art only with a highly selective and trusted group of people. Embodiments of the invention are entering a new paradigm where society and individuals need to share such data with a wider group of participants to ensure a safe and secure travel and work environment. This wider group could be authorities, businesses or transacting parties. In a post pandemic world it will become commonplace for individuals to carry their health information along with their identity information. As a consequence, many existing processes will require some modification and digitization and become part of the safety procedures in public places and during travel. Some examples of the new types of health data that will be shared may be i) test results of viral or contagious diseases ii) personal health data to identify high risk individuals iii) vaccination history. Managing these new forms of digital health data and ensuring the privacy and authenticity brings unique challenges. Embodiments of the invention have identified that blockchain technology combined with novel cryptographic methods offers unique advantages. Embodiments may be applied to sharing any form of health data and, for example, it may be focused on the CoVID-19 viral test process to demonstrate the exemplary solution. In this process, passengers entering a country submit proofs of their current health status and this will be verified by health or immigration authorities. To achieve this in a trusted manner, it is suggested a blockchain based solution that would enable physicians in each country to securely and privately record the output of medical tests on the blockchain. In a second step, when traveling to a country, each passenger can then reveal that the last tests she performed were all negative. In order to be trustworthy, this solution needs to ensure that the travelers/passengers always reveal the most recent tests, and that passengers are unable to omit some of the test results. The solution may also provide a high level of privacy for the end user. Embodiments of the invention may be an updated blockchain architecture to a blockchain-based seamless air travel system (disclosed in PCT/EP 2020/055478 and PCT/EP 2020/055479 of the applicant, not yet published, the entire contents of which are hereby incorporated by reference herein), and provide high degree of privacy and security for users through a novel zero knowledge proof construction. PCT/EP 2020/055478 and PCT/EP 2020/055479 discloses a seamless air travel system where a passenger can choose to reveal either their entire travel history or none of their travel history.

According to an embodiment of the invention, the security blockchain may do one or more of the following for each traveler of the corresponding travel segment:

The security blockchain sends to the traveler a request to share the latest t tests performed (with t the number of tests mandated by the health department of the country/region).

The blockchain receives the test access keys $h_{n-t}, \ldots, h_{n+1}$ and a proof of correctness $\pi$.

The smart contract on the blockchain verifies the proof $\pi$ and, if correct, continue to process the traveler.

The smart contract then retrieves the output of the health blockchain when given the keys $H_{n-t}, \ldots, H_{n+1}$ computed as $Hash(h_{n-t}), \ldots, Hash(h_{n+1})$.

The smart contract of the security blockchain uses this output to further verify the validity of the keys provided, in order to ensure that the traveler did not omit any test.

The smart contract of the security blockchain uses the test output of each key and apply the arrival country's policy to ensure that the traveler performed all the mandated tests.

If all the steps are performed correctly, and if the traveler's tests match the policy, the traveler is considered as healthy and non-contagious.

There are several ways how to design and further develop the teaching of the present invention in an advantageous way. To this end it is to be referred to the following explanation of embodiments of the invention by way of example, illustrated by the figure. In connection with the explanation of the embodiments of the invention by the aid of the figure, generally embodiments and further developments of the teaching will be explained.

FIG. 1 shows a schematic view illustrating a high level workflow for a method according to an embodiment of the invention.

In the embodiment, it is assumed a set of government agencies already created and are using a seamless travel system based on blockchain. This system (being a distributed ledger system) may have two different types of blockchain: one unique "global identity blockchain" that is used to provide self-sovereign identity to all the travelers, and a multitude of per segment "security blockchain" that is used to record all the information necessary to the good process of a flight segment. The security chains may also comprise the immigration department of the arrival country in order to provide pre-approval entry and facilitate traveler processing.

The embodiment further builds on this by adding a new type of blockchain, a per country "health blockchain" that is used to record the results of the different medical tests in each country. The health blockchain may comprise the main health institutes of a country, as well as the governmental health department, and finally the laboratories approved to perform the tests. The governmental health department may be the department approving laboratories and doctors (i.e. the physician entity) on the blockchain. Each licensed medical doctor/physician may further be registered on the health blockchain, without having a full node. In order to add the health passport to the per segment security chains, it is further required the national health institute of the arrival government to join this health blockchain. Each government can then issue regulations on the mandatory amount of testing and the period to do so. For example, a country could require 3 negative tests in the two weeks prior arrival, with one performed less than 48 hours before departure. Then, it may be use of smart contracts to automatize this check, allowing to ensure that all the travelers/passengers of a flight validates those requirements.

In what follows, it is first described the architecture of a seamless travel based on blockchain, and follow up with a detailed architecture of a further developed embodiment as to the added health blockchain.

Seamless Travel System

In a seamless travel system, the following minimum entities/actors may be considered:
  Immigration offices of the different countries
  Security office of each airport
  Airlines
  Travelers (external entities/actors)

All those entities/actors are registered and authenticated on the global identity blockchain. It may be differentiated the full entities/actors (the first 3 categories) that possess a full node in the blockchain system, from the external entities/actors that are only registered and are able to transact on this system as external parties without having full access. The global identity blockchain is used as a registry to authenticate any of the entities/actors in all the subsequent steps. Authentication is done through a certificate based system. Additional entities/actors can be added freely depending on the requirements. It is assumed that the bootstrap phase automatically registers the public actors (all the actors/entities except the travelers). The travelers then may register on a per usage basis. A system ensures each traveler registers at most once. This can be achieved through an Identity Based Encryption system that uses some personal data as a reference string, or using a per country (centralized) global registry that would be managed by the state (i.e. census office). Upon registration, the identity of a traveler can be verified with his passport, to ensure a correct identity. The global identity blockchain then stores only the public key $y=g^x$ of each traveler as well as the hash of their document. The per segment security blockchain is also generated and may comprise at least 5 entities for international flights (however, 3 entities may be enough in the national case): the departure and arrival airport, the departure and arrival immigration office, and finally the airline performing the segment flight.

Once a traveler decides to travel, an entry may be added on the appropriate per segment security blockchain, where all the steps of the flight travel will be recorded, such as the check-in, the pre-approval for entry by the foreign country, the baggage drop, etc. until the exit of the airport at destination. The pre-approval entry by the foreign country facilitates the handling of the travelers at the departure, as the airline can be ensured that the traveler has all the correct documents (such as visa, etc.). All this process may be managed by a smart contract that will prevent the passenger from boarding if the destination country refused entry.

Health Blockchain

It is now introduced the health blockchain that is added to the seamless travel system, wherein also the following entities/actors are added to the global identity blockchain:
  Governmental health department
  Governmentally approved laboratories
  Health institutes (external entities/actors)
  Physicians (external entities/actors)

The role of the government health department may be to issue public regulation on the requirements to enter the country directly on the global identity blockchain. Those regulation could take the form of any logical expression, such as:

Len(tests.since(today−14 days))≥3 AND Len(tests.since(today−48 hours))≥1 AND tests.ALL=negative That would require at least 3 tests in the last 2 weeks, one of which was last 48 hours, and all tests should be negative. For example, those regulation may then be automated and directly enforced at the framework layer inside the per segment security blockchain, in order to ensure proper handling of the travelers. The approved laboratories may be the only entities allowed to insert test result values, while the physicians and health institutes are the only entities allowed to collect a sample.

In order to ensure the privacy of the travelers, embodiments of the invention may introduce the following high level scheme to register a new health data record on the health blockchain. The high level steps for a traveler according to embodiments of the invention may be the following, as illustrated in FIG. 1:

1. Authenticating the traveler at the physician's office.
2. The physician verifies the traveler's credential with the help of the global identity blockchain.
3. The traveler then provides access keys $h_n$, $h_{n-1}$ as (additional) secret information that will be used to register her results on the health blockchain, along with a proof of correctness $\pi_n$. The secret information can be decomposed into $<h_n, h_{n-1}>$.
4. The physician ensures that the proof $\pi_n$ is correct and that the access keys $h_n$, $h_{n-1}$ have not been used yet using the health blockchain.
5. The physician can then take a sample from the traveler/patient.
6. The sample is recorded on the health blockchain using the a hash $H_n$ of the access key $h_n$ provided by the traveler and verified beforehand. Thus, $H_n$ is the hashed access key.
7. The sample is sent for analysis to the laboratory.
8. The laboratory updates the record for the traveler and adds the result of the test.

All the steps 1. to 4. may be performed before the appointment through a mobile application service. The results stored on the health blockchain can be very succinct, such as "Viral test Positive/Negative", while the full tests results will still be provided to the patient's physician.

In this setup, it is important for the data stored on the health blockchain to be Secure: one cannot claim the tests of another traveler as her own
Privacy preserving: an external party should not be able to determine to whom the test records belongs to
Complete: a traveler should not be able to selectively disclose the tests he wants to share, or a malicious traveler could try to disclose only false positive tests.

Figure 2:
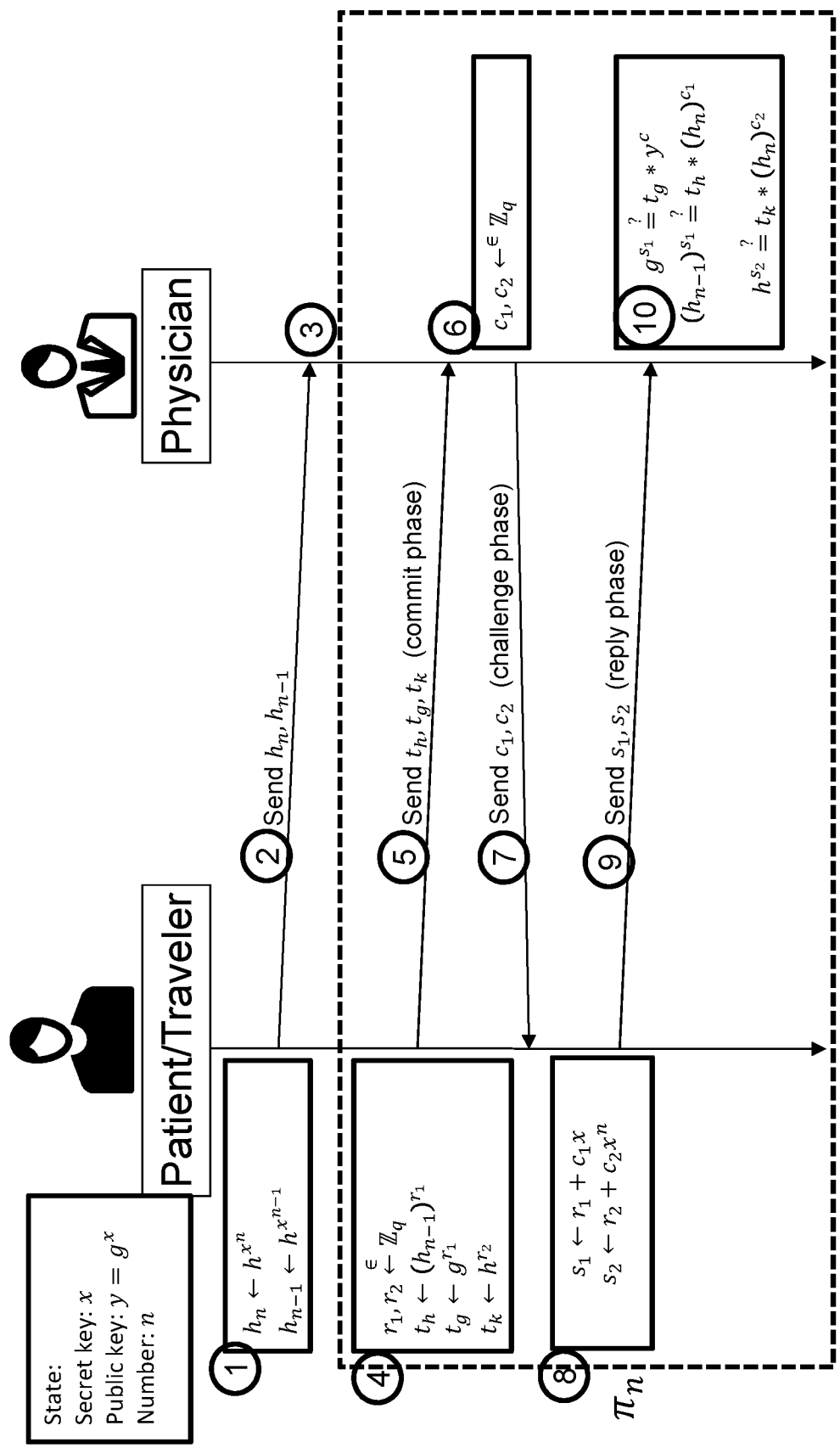
FIG. 2 is a schematic view illustrating a workflow of a zero knowledge proof for a method according to an embodiment of the invention.

FIG. 2 shows a schematic view illustrating a workflow of a zero knowledge proof for a method according to an embodiment of the invention. In order to achieve the aforementioned requirements for the setup of the high level scheme illustrated by FIG. 1, embodiments of the invention may use a novel zero knowledge proof construction detailed as follows:

The assumed model according to an embodiment may consider a multiplicative cyclic group G of prime order q with the generators g and h, where q is a big prime number. A generator g in a cyclic group with an operation * is an element with the property of iterating through all the elements of the group when subsequently applying the group operation on itself. In other words, every element of the group can be expressed using the generator (i.e. g) and the number of time the operation * should be performed (i.e. $g^{1, 2, 3}, \ldots$). It is further made use of two different hash functions Hash and Hash' that achieve all the properties of a cryptographic hash function. For example, Hash(x) and Hash'(x) may be instantiated as sha256(x) and sha256("prefix"+x) respectively, for any given "prefix" string. For simplicity, it is used the notation of Hash and Hash' in the following.

The private key x of a traveler is drawn randomly $x \in \mathbb{Z}_q$ and the matching public key is $y \leftarrow g^x$. The traveler's application further keeps track of a variable n that starts at 1: $n \leftarrow 1$.

The hashed secret information, i.e. the hashed access keys, being used on the blockchain actually comprise two parts: one hashed access key $H_n$ that is used when inserting a health data record (step 6 and 8 of the high level scheme illustrated by FIG. 1) on the health blockchain, and a hashed previous access key $H'_{n-1}$. The hashed secret information can therefore be decomposed into $<H_n, H_{n-1}'>$.

To generate the hashed access keys, the traveler first computes the access keys $h_n$, $h_{n-1}$ as secret information by $h_n = h^{x^n}$ and $h_{n-1} = h^{x^{n-1}}$ given her private key x. Each $h^{x^{1,n}}$ are indistinguishable from a value $h^y$ for a random y under the Decisional Diffie-Hellman assumption. They are therefore unlinkable and can be used as keys in the blockchain key-value store. The hashed secret information, i.e. the hashed access keys are then computed as Hash($h^{x^n}$) and Hash'($h^{x^{n-1}}$). The traveler then only needs to generate $\pi_n$ as a proof of same exponent between $h^{x^n}$ in base $h^{x^{n-1}}$ and her public key $g^x$ in base g. The traveler can then simply send the values $h_n$, $h_{n-1}$ and $\pi_n$ to the verifier.

The workflow of the zero knowledge proof depicted in the embodiment of FIG. 2 may be specified as follows:

1. The traveler first generates the values $h_n$ and $h_{n-1}$ as access keys.
2. The traveler sends the access keys $h_n$, $h_{n-1}$ to the physician entity.
3. Upon reception of those values, the physician entity checks that $H_{n-1} = \text{Hash}(h_{n-1})$ has already been used on the health blockchain and that $H_n = \text{Hash}(h_n)$ has not been used yet. For simplicity this step is merely indicated in FIG. 2.
4. The traveler then starts the zero knowledge proof $\pi_n$ by generating three commitments: $t_h$, $t_g$ and $t_k$ using $r_1$, $r_2$ drawn uniformly at random from $\mathbb{Z}_q$
5. The traveler sends the commitments $t_h$, $t_g$ and $t_k$ to the physician entity.
6. The physician entity generates challenges $c_1$, $c_2$ drawn uniformly at random from $\mathbb{Z}_q$
7. The physician entity sends $c_1$, $c_2$ to the traveler
8. The traveler generates the responses $s_1$ as $s_1 \leftarrow r_1 + c_1 * x$ and $s_2$ as $s_2 \leftarrow r_2 + c_2 * x^n$
9. The traveler sends the response $s_1$, $s_2$ to the physician entity
10. The physician entity accepts the proof $\pi_n$ if and only if both $g^{s_1}$ is indeed equal to $t_g * y^{c_1}$ and $(h_{n-1})^{s_1}$ is indeed equal to $t_h * (h_n)^{c_1}$. The physician further checks that $h^{s_2}$ is indeed equal to $t_k * (h_n)^{c_2}$. If this is the case, then the physician entity can be ensured that the values $h_n$ and $h_{n-1}$ sent by the traveler are correct.

Since the access key $h_n$ is unique for a given private key x, if the physician entity is ensured that access key $h_n$ has been computed correctly, the physician entity knows that the traveler is not trying to hide some data.

Adding Result to the Health Blockchain

Once the physician entity verified the proof $\pi_n$ for the access keys $h_n$, $h_{n-1}$, the physician entity can issue a first register transaction that records the hashed access key $H_n \leftarrow \text{Hash}(h_n)$, the previous access key $H_{n-1}' \leftarrow \text{Hash}'(h_{n-1})$ and the sample number that will be used by the laboratory entity to identify the record. The register transaction may be performed as follows:

Add Record Transaction (sent to the health blockchain):
<$H_n$, $H_{n-1}'$, sampleNumber, timestamp, sig> where sig represents the signature over all the previous field using the private key of the physician entity in order to attest authenticity and integrity. It is stored using $H_n$ as the key, and <$H_{n-1}'$, sampleNumber, timestamp> as the value in the key-value store of the blockchain. The timestamp may be optional. The timestamp may include time information that can be used to record when the sample of the traveler/patient was taken. Thus, the timestamp may include time information that can be used to record when a test or vaccine was performed.

Hence, the health blockchain can receive a new sample of the traveler of the form <$H_n$, $H_{n-1}'$, sampleNumber, sig> and stores it against the hashed access key $H_n$.

Once the laboratory entity has the results from the test, the laboratory entity can perform the update transaction as follows:

Update Record Transaction (sent to the health blockchain):
<sampleNumber, TEST_RESULT, sig> where TEST_RESULT is the result of the viral test, and sig is the signature over the previous field using the private key of the laboratory entity. The final record has as key $H_n$ (which is the hashed access key) and the matching value is <$H_{n-1}'$, TEST_RESULT>

Thus, the health blockchain receives an update of the form <sampleNumber, TEST_RESULT, sig> and updates the record for the key $H_n$ to have it as: $H_n \rightarrow$<$H_{n-1}'$, TEST_RESULT, timestamp>

Figure 3:
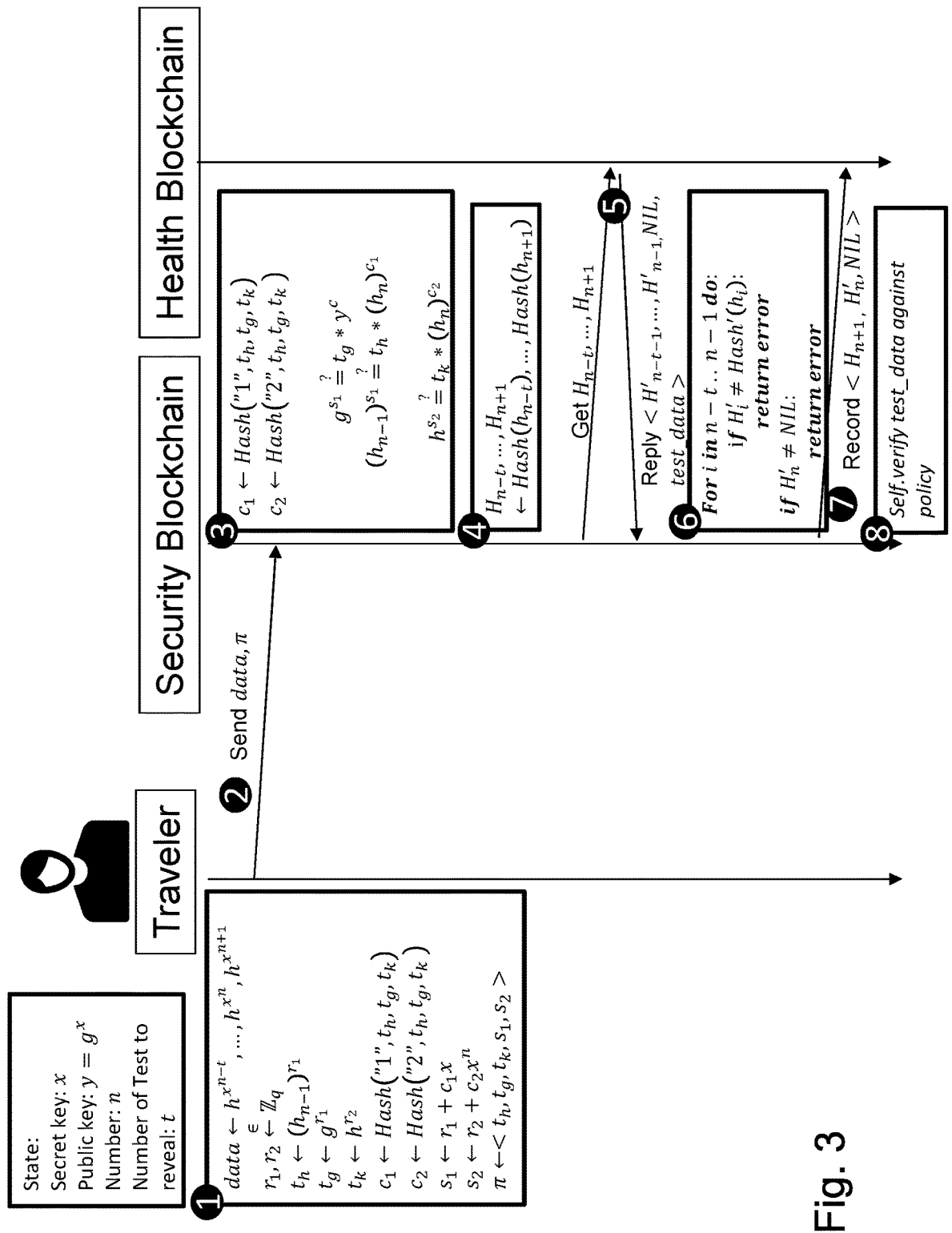
FIG. 3 is a schematic view illustrating a workflow for sharing health data of a traveler in accordance with an embodiment of the invention.

FIG. 3 shows a schematic view illustrating a workflow for sharing health data of a traveler in accordance with an embodiment of the invention.

Proving Healthiness:

For instance, it may be assumed that the traveler performed 3 tests in the last 2 weeks, one of which was done in the latest 48 hours before departure of her plane. When the traveler checks in, e.g. using the mobile application on her smartphone, the traveler will receive a request to share health data, which may be performed the following way:

In order to share the health data information, the user may go through the following steps, according to the embodiment illustrated in FIG. 3:

1. The traveler first generates all the access keys and the proof required to validate those keys. It is done as follows, assuming the traveler has to reveal information on the t last tests, which may correspond to the t last health data records of the traveler stored in the health blockchain:
   I. Compute access keys $h_{n-t} \ldots h_{n+1} \leftarrow h^{x^{n-t}} \ldots h^{x^{n+1}}$
   II. data$\leftarrow [h_{n-t}, \ldots, h_{n+1}]$
   III. Compute $\pi$ by analogy with the proof procedure of FIG. 2, however now using the Fiat-Shamir transformation to make it uninteractive. It requires computing the challenges $c_1$, $c_2$ as the hash of the commitments $t_h$, $t_g$ and $t_k$. The steps are as follows:
       i. Pick $r_1$, $r_2$ at random uniformly in $\mathbb{Z}_q$
       ii. Create commitments $t_h \leftarrow (h_{n-1})^{r_1}$, $t_g \leftarrow g^{r_1}$ and $t_k \leftarrow h^{r_2}$
       iii. Compute challenges $c_1 \leftarrow \text{Hash}("1", t_h, t_g, t_k)$ and $c_2 \leftarrow \text{Hash}("2", t_h, t_g, t_k)$
       iv. Compute response messages $s_1 \leftarrow r_1 + c_1 * x$ and $s_2 \leftarrow r_2 + c_2 x^n$
       v. Set proof $\pi$ as $\pi \leftarrow$ <$t_h$, $t_g$, $t_k$, $s_1$, $s_2$>
2. The traveler can then send the access keys and the proof to the security blockchain corresponding to her flight segment
3. The smart contract on the security blockchain first verifies the validity of the proof:
   I. Recompute $c_1 \leftarrow \text{Hash}("1", t_h, t_g, t_k)$ and $c_2 \leftarrow \text{Hash}("2", t_h, t_g, t_k)$
   II. Verify $g^{s_1} \stackrel{?}{=} t_g * y^{c_1}$, $g^{s_1} \stackrel{?}{=} t_g * y^{c_1}$ and $h^{s_2} \stackrel{?}{=} t_k * (h_n)^{c_2}$ using the public key y of the traveler.
   The security blockchain only needs to verify the link between the new value $h_{n+1}$ and the latest value $h_n$ to be correct, as all the previous values are already linked in the health blockchain through their hashes: if one has knowledge of $h_n$ and $h_{n-1}$, one can verify the link between them by requesting the value for the hashed access key $\text{Hash}(h_n)$, which returns the hashed previous access key $H_{n-1}'$. The verification of the link is then simply done by ensuring that $H_{n-1}' \stackrel{?}{=} \text{Hash}'(h_{n-1})$
4. From the values $h_{n-t} \ldots h_{n+1}$ as access keys, the smart contract of the security blockchain computes the hashed access keys as values $H_{n-t} \ldots H_{n+1} \leftarrow \text{Hash}(h_{n-t}) \ldots \text{Hash}(h_{n+1})$
5. The smart contract of the security blockchain then requests the data (such as health data records) associated with those hashed access keys from the health blockchain. The smart contract of the security blockchain receives in return <$H'_{n-t-1}, \ldots, H'_{n-1}, H_n'$, test_data>
6. The smart contract of the security blockchain first verifies the links between all the previous values to ensure that the user did not skip one test data:
   I. *For* i *in* n−t . . . n−1 *do*
      *if* $H_i' \neq \text{Hash}'(h_i)$
         Error: access keys provided by the traveler are not consecutive/continuous
   The smart contract then checks that the latest value ($h_{n+1}$) has not been used yet:
   II. *if* $H_n' \neq \text{NIL}$:
      Error: The access key $h_{n+1}$ provided by the traveler was not the latest.
   The smart contract of the security blockchain may verify that the oldest health data record (of the requested data) is within a predetermined time frame. For instance, the smart contract of the security blockchain may verify that the oldest health data record is at least so old as a requested time frame. For example, if one requests 2 weeks of test results, the oldest record may be at least 2 weeks old. Thus, it may be provided that the oldest result should be at least 2 weeks old to make sure that all the test of the last 2 weeks were received.
7. The smart contract now "spends" the latest access key as hashed access key $H_{n+1}$ to show that it was revealed properly.
8. The smart contract is now ensured of the validity of the access keys provided and can trust the test_data results provided by the health blockchain. It then simply verifies that the test data satisfies the policy setup by the arrival health department. This policy can be retrieved beforehand from the global identity blockchain.

The advantage of embodiments of the invention is that it is computationally infeasible for a client to forge fake health documents as it is assumed that the digital signature cryptography used in this embodiment to remain secure. Furthermore, the arrival government is ensured that the traveler is showing all the latest tests or health data records and is not obfuscating some tests or health data that are not favorable to the traveler.

Furthermore, embodiments of the invention provide perfect privacy for end user against third parties, as they are unable to extract any information from the health blockchain.

In the embodiment illustrated by FIG. 3, it is detailed how the solution could be used for sharing viral test results in a privacy preserving manner over a defined period without the possibility to omit any result. However, this methodology may be used to share any type of health data such as tests for viral flus, vaccination history or general medical health results. This can be done easily by simply assigning one generator for each type of test (i.e. the generator h is used for covid-19 tests, the generator i is used for flue tests, the generator j for the vaccination history, etc.). The system can then enforce to get all the latest values for each of those generators. Then, upon document sharing request, the traveler will have to make one proof for each type of test required by the arrival country. Since the discrete logarithm of the generators are not known, the tests remain completely unlinkable, even if the traveler reveals all the tests he performed for one disease.

Many modifications and other embodiments of the invention set forth herein will come to mind to the one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A method for supporting sharing of digital health data of travelers in a travel environment, wherein an identity of a traveler is managed using a distributed ledger system, wherein the distributed ledger system includes a global identity blockchain, several security blockchains and a health blockchain,
   wherein the global identity blockchain is employed as a registry to authenticate entities of the distributed ledger system,
   wherein a security blockchain of the several security blockchains is employed for a predetermined travel segment, such that the security blockchain is accessible by entities of the distributed ledger system that are involved in the predetermined travel segment,
   wherein the health blockchain is employed for sharing health data of the travelers in a key-value store of the health blockchain, wherein a health data record is stored against a hashed access key, wherein the health data record includes a hashed previous access key and health data information,
   the method comprising:
      sending, from the security blockchain to a traveler, a request to share a predetermined number of health data records;
      receiving, by the security blockchain, consecutive access keys for the requested health data records and a zero knowledge proof from the traveler;
      verifying, by the security blockchain, the zero knowledge proof received from the traveler, wherein the zero knowledge proof is utilized to validate a latest access key of the access keys provided by the traveler;
      upon successful verification of the zero knowledge proof, retrieving, by the security blockchain, the health data records from the health blockchain based on hashed access keys, wherein the hashed access keys are generated from the access keys provided by the traveler;
      verifying, by the security blockchain, access keys provided by the traveler using hashed previous access keys included in the retrieved health data records, in order to determine whether the traveler has provided the access keys required for the health data records as requested.

2. The method according to claim 1, wherein a previous access key, which is included as hash in a health data record of the traveler, represents an access key for the previous health data record of the traveler on the health blockchain.

3. The method according to claim 1, wherein a first hash function is used to compute the hashed access keys that are used as keys for health data records in the key-value store of the health blockchain, and wherein a second hash function is used to compute hashed previous access keys that are stored as values for health data records in the key-value store of the health blockchain.

4. The method according to claim 1, wherein the traveler provides a physician entity with secret information and a zero knowledge proof for the secret information, wherein the zero knowledge proof is used to verify the secret information by the physician entity, and wherein the secret information is used to register a new health data record on the health blockchain.

5. The method according to claim 4, wherein the secret information includes an access key and a previous access key.

6. The method according to claim 4, wherein the physician entity verifies that the secret information has not been used yet on the health blockchain.

7. The method according to claim 4, wherein a multiplicative cyclic group (G) of prime order (q) with public generators (g) and (h) is used for sharing health data of the traveler on the health blockchain,
   wherein a private key (x) of the traveler is picked as a random (x $\in \mathbb{Z}_q$) and a public key of the traveler is y=$g^x$, wherein $\mathbb{Z}_q$ is a multiplicative group of integers that are co-prime with q,
   wherein the traveler keeps track of a variable (n) referring to a total number of health data records of the traveler, and
   wherein the traveler computes the access key for the nth health data record as $h_n = h^{x^n}$ and a previous access key as $h_{n-1} = h^{x^{n-1}}$ based on the private key (x) of the traveler.

8. The method according to claim 7, wherein the zero knowledge proof for the secret information provided by the traveler to the physician entity comprises:
   generating, by the traveler, commitments $t_h = (h_{n-1})^{r_1}$, $t_g = g^{r_1}$ and $t_k = g^{r_2}$ using $r_1, r_2$ drawn uniformly at random from $\mathbb{Z}_q$,
   sending, by the traveler, the commitments $t_h$, $t_g$ and $t_k$ to the physician entity,
   sending, by the physician entity, challenges $c_1$, $c_2$ to the traveler, wherein the physician entity generates the challenges $c_1$ and $c_2$ drawn uniformly at random from $\mathbb{Z}_q$,
   sending, by the traveler, responses $s_1$, $s_2$ to the physician entity, wherein the traveler generates the responses $s_1$, $s_2$ as $s_1 = r_1 + c_1 * x$ and $s_2 = r_2 + c_2 x^n$,
   wherein the physician entity accepts the zero knowledge proof, if $g^{s_1}$ is equal to $t_g * y^{c_1}$ and $(h_{n-1})^{s_1}$ is equal to $t_h * (h_n)^{c_1}$ and $h^{s_2}$ is equal to $t_k * (h_n)^{c_2}$.

9. The method according to claim 4, wherein the health blockchain receives from the physician entity a register transaction for adding a new health data record for the traveler to the health blockchain,
   wherein the register transaction comprises a hashed access key, a hashed previous key and health data information,
   wherein the new health data record is stored against the hashed access key, and
   wherein the hashed previous key and the health data information is stored as value of the new health data record in the key-value store of the health blockchain.

10. The method according to claim 9, wherein the health data information includes a sample number that is used to identify the new health data record,
    wherein the new health data record on the health blockchain is updated upon receiving an update transaction such that the health data record comprises updated health data information.

11. The method according to claim 10, wherein:
    the sample number is used to identify the new health data record by a laboratory entity, and
    wherein the new health data record on the health blockchain is updated upon receiving an update transaction by the laboratory entity.

12. The method according to claim 9, wherein the health data information and/or the updated health data information includes information about a viral test result of the traveler.

13. The method according to claim 9, wherein the health data information and/or the updated health data information includes information about health data of the traveler, vaccination information, and/or a medical health test result.

14. The method according to claim 1, further comprising:
    verifying, by the security blockchain, that the health data of the traveler satisfies a predetermined policy setup.

15. The method according to claim 1, wherein the consecutive access keys that are provided by the traveler represent together with the associated retrieved health data records a time frame.

16. The method according to claim 1, wherein a physician entity verifies credential information provided by the traveler using the global identity blockchain in order to authenticate the traveler at the physician entity.

17. A distributed ledger system for supporting sharing of digital health data of travelers in a travel environment, wherein the distributed ledger system comprises:
    a global identity blockchain, several security blockchains and a health blockchain,
    wherein the global identity blockchain is employed as a registry to authenticate entities of the distributed ledger system,
    wherein a security blockchain of the several security block chains is employed for a predetermined travel segment, such that the security blockchain is accessible by entities of the distributed ledger system that are involved in the predetermined travel segment,
    wherein the health blockchain is employed for sharing health data of the travelers in a key-value store of the health blockchain, wherein a health data record is stored against a hashed access key, wherein the health data record includes a hashed previous access key and health data information,
    wherein a security blockchain is configured to send to a traveler a request to share a predetermined number of health data records,
    wherein the security blockchain is configured to receive consecutive access keys for the requested health data records and a zero knowledge proof from the traveler,
    wherein the security blockchain is configured to verify the zero knowledge proof received from the traveler, wherein the zero knowledge proof is utilized to validate a latest access key of the access keys provided by the traveler,
    wherein, upon successful verification of the zero knowledge proof, the security blockchain is configured to retrieve the health data records from the health blockchain based on hashed access keys, wherein the hashed access keys are generated from the access keys provided by the traveler,
    wherein the security blockchain is configured to verify access keys provided by the traveler using hashed previous access keys included in the retrieved health data records, in order to determine whether the traveler has provided the access keys required for the health data records as requested.

* * * * *